(12) United States Patent
Rouan et al.

(10) Patent No.: US 9,920,332 B2
(45) Date of Patent: Mar. 20, 2018

(54) **HYBRID *BRASSICA* PLANTS AND METHODS FOR PRODUCING SAME**

(71) Applicant: Bayer CropScience NV, Diegem (BE)

(72) Inventors: Dominique Rouan, Sint-Denijs-Westrem (BE); Greta De Both, Wetteren (BE)

(73) Assignee: Bayer CropScience NV, Diegem (BE)

( * ) Notice: Subject to any disclaimer, the term of this patent is extended or adjusted under 35 U.S.C. 154(b) by 51 days.

(21) Appl. No.: 14/785,266

(22) PCT Filed: Apr. 16, 2014

(86) PCT No.: PCT/EP2014/057770
§ 371 (c)(1),
(2) Date: Oct. 16, 2015

(87) PCT Pub. No.: WO2014/170387
PCT Pub. Date: Oct. 23, 2014

(65) Prior Publication Data
US 2016/0068859 A1 Mar. 10, 2016

(30) Foreign Application Priority Data

Apr. 19, 2013 (EP) .................................... 13164421

(51) Int. Cl.
*A01H 1/02* (2006.01)
*C12N 15/82* (2006.01)
*A01H 5/10* (2006.01)

(52) U.S. Cl.
CPC ........... *C12N 15/8287* (2013.01); *A01H 1/02* (2013.01); *A01H 5/10* (2013.01); *C12N 15/8231* (2013.01); *C12N 15/8261* (2013.01); *C12N 15/8289* (2013.01)

(58) Field of Classification Search
None
See application file for complete search history.

(56) References Cited

U.S. PATENT DOCUMENTS

| | | |
|---|---|---|
| 5,689,041 A | 11/1997 | Mariani et al. |
| 5,792,929 A | 8/1998 | Mariani et al. |

FOREIGN PATENT DOCUMENTS

| | | |
|---|---|---|
| EP | 0 344 029 A1 | 11/1989 |
| EP | 0 534 858 A1 | 3/1993 |
| WO | WO 96/26283 A1 | 8/1996 |
| WO | WO 01/31042 A2 | 5/2001 |
| WO | WO 01/41558 A1 | 6/2001 |
| WO | WO 2005/003381 A1 | 1/2005 |

OTHER PUBLICATIONS

Rao et al. International Journal of Tropical Agriculture 11(1): 14-19 (1993).*

De Block et al., "Engineered fertility control in transgenic *Brassica napus* L.: Histochemical analysis of another development," 1993, Planta, vol. 189: pp. 218-225.
De Block et al., "Engineering herbicide resistance in plants by expression of a detoxifying enzyme," 1987, EMBO Journal, vol. 6, No. 9: pp. 2513-2518.
Depicker et al., "Nopaline Synthase: Transcript Mapping and DNA Sequence," 1982, Journal of Molecular and Applied Genetics, vol. 1, No. 6: pp. 561-573.
Dhaese et al., "Identification of sequences involed in the polyadenylation of higher plant nuclear transcripts using Agrobacterium T-DNA genes as models," 1983, The EMBO Journal, vol. 2, No. 3: pp. 419-426.
Gielen et al., "The complete nucleotide sequence of the TL-DNA of the Agrobacterium tumefaciens plasmid pTiAch5," 1984, The EMBO Journal, vol. 3, No. 4: pp. 835-846.
Hartley, "Barnase and Barstar Expression of Its Cloned Inhibitor Permits Expression of a Cloned Ribonucleotase," 1988, Journal of Molecular Biology, vol. 202: pp. 913-915.
International Search Report of PCT/EP2014/057770 dated July 28, 2014.
Krebbers et al., "Four genes in two diverged subfamilies encode the ribulose-1,5-bisphosphate carboxylase small subunit polypeptides of *Arabidopsis thaliana*," 1988, Plant Molecular Biology, vol. 11: pp. 745-759.
Mariani et al., "Induction of male sterility in plants by a chimaeric ribonuclease gene," 1990, Nature, vol. 347: pp. 737-741.
Michelmore et al., "Identification of markers linked to disease-resistance genes by bulked segregant analysis: A rapid method to detect markers in specific genomic regions by using segregating populations," 1991, Proc. Natl. Acad. Sci. USA, vol. 88: pp. 9828-9832.
Parkin et al., "Identification of the A and C genomes of amphidiploid *Brassica napus* (oilseed rape)," 1995, Genome, vol. 38: pp. 1122-1131.
Seurnick et al., "The nucleotide sequence of an anther-specific gene," 1990, Nucleic Acids Research, vol. 18, No. 11: p. 3403.
Sharpe et al., "Frequent nonreciprocal translocations in the amphidiploid genome of oilseed rape (*Brassica napus*)," 1995, Genome, vol. 38: pp. 1112-1121.
Thompson et al., "Characterization of the herbicide-resistance gene bar from Streptomyces hygroscopicus," 1987, The EMBO Journal, vol. 6, No. 9: pp. 2519-2523.
Velten et al., "Selection-expression plasmid vectors for use in genetic transformation of higher plants," 1985, Nucleic Acids Research, vol. 13, No. 19: pp. 6981-6998.
Vos et al., "AFLP: a new technique for DNA fingerprinting," 1995, NAR, vol. 23, No. 21: pp. 4407-4414.

(Continued)

*Primary Examiner* — David T Fox
(74) *Attorney, Agent, or Firm* — Arent Fox LLP

(57) ABSTRACT

Provided are transgenic *Brassica* plants, plant material and seeds, particularly oilseed rape plants, characterized in that these plants harbor a novel combination of two specific transformation events, namely MS-B2 comprising a male-sterility transgene and RF-BN1 comprising a fertility-restoration transgene. Also provided are pairs of *Brassica* plants comprising each one of the events, and the use thereof in the production of hybrid seed.

13 Claims, 2 Drawing Sheets

(56) References Cited

OTHER PUBLICATIONS

Declaration from Dominique Rouan submitted in EP Application No. 14721239.3 dated Oct. 12, 2017, pp. 1-6.
Bisht et al., "A two gene—two promoter system for enhanced expression of a restorer gene (barstar) And development of improved fertility restorer lines for hybrid seed production in crop plants," Molecular Breeding, vol. 14, 2004, pp. 129-144.
Decision Document 96-17: Determination of Environmental Safety of Plant Genetic Systems Inc.'s. (PGS) Novel Hybridization System for Rapeseed (*Brassica napus* L.), Canadian Food Inspection Agency, http://www.inspection.gc.ca/english/plaveg/pdo/dd9617e.shtml, last accessed Oct. 23, 2001.
Letter dealing with Oral Proceedings, European Patent application EP 14 721 239.3 in the name of Bayer CropScience N.V. dated Oct. 16, 2017, pp. 1-18.
Risk Assessment and Risk Management Plan for DIR 021/2002, Application for license for dealings involving an intentional release into the environment, Commercial release of genetically modified (InVigor® hybrid) canola, Jul. 2003, pp. 1-31.
Risk Assessment and Risk Management Plan for DIR 032/2002, Application for license for dealings involving an intentional release into the environt., Field trial—Seed increase and field evaluation of herbicide tolerant genetically modified canola incorporating a hybrid breeding system, Mar. 2004, pp. 1-101.
Risk Assessment and Risk Management Plan for DIR 057/2004, Application for license for dealings involving an intentional release into the environment, Field trials of genetically modified hybrid, herbicide tolerant Indian mustard (*Brassica juncea*), Jun. 2005, pp. 1-107.
Risk Assessment and Risk Management Plan for DIR 069/2006, Limited and controlled release of GM herbicide tolerant hybrid *Brassica napus* and *Brassica juncea*, Mar. 2007, pp. 1-30.
Risk Assessment and Risk Management Plan for DIR 104, Limited and controlled release of canola and Indian mustard genetically modified for herbicide tolerance and/or a hybrid breeding system, Sep. 2010, pp. 1-35.
Risk Assessment and Risk Management Plan for DIR 108, Commercial release of canola genetically modified for herbicide tolerance and a hybrid breeding system (InVigor®, x Roundup Ready® canola), Dec. 2011, pp. 1-34.

* cited by examiner

SEQUENCE LISTING

```
<160> NUMBER OF SEQ ID NOS: 10

<210> SEQ ID NO 1
<211> LENGTH: 415
<212> TYPE: DNA
<213> ORGANISM: Artificial
<220> FEATURE:
<223> OTHER INFORMATION: 5' border flanking region of elite event MS-B2

<400> SEQUENCE: 1
gtcgagtttg gtgttcatga ttttgggttt tgactcttca ccattacata ttgaaactct      60
tacggatgag aacaactcac aagcattaat catgttcata taaatatatg tacattatac     120
gtatatatac acgtatacaa atagtagcga agaaatccat gtaaagcagc aggggcacc      180 atggtttcaa gtattatata attataatta taattatggt aggatgtaca tggccgataa     240
gaaaaggcaa tttgtagatg ttaattccca tcttgaaaga aatatagttt aaatatttat     300
tgataaaata acaagtcagg tattatagtc caagcaaaaa cataaattta ttgatgcaag     360
tttaaattca gaaatatttc aataactgat tatatcagct ggtacattgc cgtag          415

<210> SEQ ID NO 2
<211> LENGTH: 416
<212> TYPE: DNA
<213> ORGANISM: Artificial
<220> FEATURE:
<223> OTHER INFORMATION: 3' border flanking region of elite event MS-B2

<400> SEQUENCE: 2
ctacggcaat gtaccagctg atataatcag ttattgaaat atttctgaat ttaaacttgc      60
atcaataaaw ttatgttttt gcttggacta taatacctga cttgttattt tatcaataaa    120
tatttaaact atatttcttt caagatggga attaacatct acaaattgcc ttttcttatc    180
```

```
gaccatgtac atcctaccat aattataatt ataattatat aatactgaaa ccatggtgcc      240
ccctgctgct ttacatggat ttctccgcta ctatttgtat acgtgtatat ataccgtata      300
atgtacatat atttatatga acatgattaa tgcttgtgag ttgttctcat ccgtaagagt      360
ttcaatatgt aatggtgaag agtcaaaacc caaaatcatg aacacccaaa ctcgat          416

<210> SEQ ID NO 3
<211> LENGTH: 23
<212> TYPE: DNA
<213> ORGANISM: Artificial
<220> FEATURE:
<223> OTHER INFORMATION: Oligonucleotide primer 1 for detection of MS-B2

<400> SEQUENCE: 3
gaaatccatg taaagcagca ggg                                              23

<210> SEQ ID NO 4
<211> LENGTH: 21
<212> TYPE: DNA
<213> ORGANISM: Artificial
<220> FEATURE:
<223> OTHER INFORMATION: oligonucleotide primer 2 for detection of MS-B2

<400> SEQUENCE: 4
gcttggacta taatacttga c                                                21

<210> SEQ ID NO 5
<211> LENGTH: 694
<212> TYPE: DNA
<213> ORGANISM: Artificial
<220> FEATURE:
<223> OTHER INFORMATION: 5' flanking region of RF-BN1

<400> SEQUENCE: 5
ggttttcgga ggtccgagac gagttcaaaa atacatttta cataatatat ttttcatata      60
tatatatata taacattc aaaagtttga attattcat aaacgttttc taaatttct          120 tcaccaaaat tttataaact aaaatttta aatcatgaac aaaaagtatg aatttgtaat       180
ataaatacaa agatacaaat ttttgattga atattggta gctgtcaaaa agtaaatct       240 tagaatttaa attaactata gtaaactata tattgaaaat attataaatt tttatcaaat     300
tctcataaat atataaaata aatctaactc atagcatata aaaagaagac taatgtggat     360
caaaatattt acagttttttt agaagtagaa tctttatagt tttatttaaa atatagcaaa    420
aatgatcaca aacctagtta ctttaaccag aagtccaatt caaaatcaaa taaaaataaa     480
aatctatcta aaaaaatatg ttaactacca tgcaaaagta ttttttttg taattagaaa      540 ccctgaaatt tgtacaaaac ttggaccccct aggtaaatgc ctttttcatc tcgcgataag    600
aaaaggcaat ttgtagatgt taattcccat cttgaaagaa atatagttta aatattatt      660 gataaaataa caagtcaggt attatagtcc aagc                                 694

<210> SEQ ID NO 6
<211> LENGTH: 1279
<212> TYPE: DNA
<213> ORGANISM: Artificial
<220> FEATURE:
<223> OTHER INFORMATION: 3' flanking region of RF-BN1

<400> SEQUENCE: 6
gggggttttt tttttgatc aataactttg ttgggcttat ggtcgataag cgtgcgcatg       60
tctgatggta catgctaaat gctatatttc tgtttaaagt gttaaaatca ttttctgatg      120
```

```
gaactaaatc cagttttaag agtaactgac aagtacaatt aagcacaaca ataaaatagt    180
agtaattggc atctttgatt gttaaatatc aaacaataaa gttcaaaaaa aaataccaac    240
ccaataatga agacttggcg gagacagtgc cgtgcgaagg ttttcggagg tccgagacga    300
gttcaaaaat acattttaca taatatattt ttcatatata tatatatata taacattcaa    360
aagtttgaat tattacataa acgttttcta aattttcttc accaaaattt tataaactaa    420 aattttaaa tcatgaacaa aaagtatgaa tttgtaatat aaatacaaag atacaaattt     480
ttgattgaaa tattggtagc tgtcaaaaaa gtaaatctta gaatttaaat taactatagt    540
aaactatata ttgaaaatat tataaatttt tatcaaattc tcataaatat ataaaataaa    600
tctaactcat agcatataaa aagaagacta atgtggatca aaatatttac agtttttttag   660 aagtagaatc tttatagttt tatttaaaat atagcaaaaa tgatcacaaa cctagttact    720
ttaaccagaa gtccaattca aaatcaaata aaaataaaaa tctatctaaa aaaatatgtt    780
aactaccatg caaaagtatt ttttttttgta attagaaacc ctgaaatttg tacaaaactt   840
ggacccctag gtaaattccc tagaaagtat cctattagcg tcgacaaact gttgctcata    900
tttttctctc cttactttat atcatacact aatataaaaa gatgatctaa ttaattattc    960
atttccatgc tagctaattc aagaaaaaga aaaaaaactt attatctaaa cttatattcg   1020
agcaacacct cggagataac aggatatatg tcattaatga atgcttgaac tcatctcgcg   1080
aactcatctc gcatcgctta tagccacaaa gatccaaccc ctctcttcaa tcatatatca   1140
gtagtacaat acaaatagat attgtgagca catatgccgt ctagtactga tgtgtatatg   1200
tagaggagcc gcaaatgttt agtcactcca acaaatgagc atgaccacgc atcttctgat   1260
gatgtacagc cgtccctttt                                               1279

<210> SEQ ID NO 7
<211> LENGTH: 21
<212> TYPE: DNA
<213> ORGANISM: Artificial
<220> FEATURE:
<223> OTHER INFORMATION: Oligonucleotide primer 1 for detection of
      RF-BN1

<400> SEQUENCE: 7
tcatctacgg caatgtacca g                                               21

<210> SEQ ID NO 8
<211> LENGTH: 20
<212> TYPE: DNA
<213> ORGANISM: Artificial
<220> FEATURE:
<223> OTHER INFORMATION: Oligonucleotide primer 2 for detection of
      RF-BN1

<400> SEQUENCE: 8 tggacccta ggtaaatgcc                                                  20

<210> SEQ ID NO 9
<211> LENGTH: 4832
<212> TYPE: DNA
<213> ORGANISM: Artificial
<220> FEATURE:
<223> OTHER INFORMATION: Plasmid pTHW118

<400> SEQUENCE: 9
aattacaacg gtatatatcc tgccagtact cggccgtcga actcggccgt cgagtacatg    60
```

```
gtcgataaga aaaggcaatt tgtagatgtt aattcccatc ttgaaagaaa tatagtttaa      120
atatttattg ataaaataac aagtcaggta ttatagtcca agcaaaaaca taaatttatt      180
gatgcaagtt taaattcaga aatatttcaa taactgatta tatcagctgg tacattgccg      240
tagatgaaag actgagtgcg atattatgtg taatacataa attgatgata tagctagctt      300
agctcatcgg gggatcctag acgcgtgaga tcagatctcg gtgacgggca ggaccggacg      360
gggcggtacc ggcaggctga agtccagctg ccagaaaccc acgtcatgcc agttcccgtg      420
cttgaagccg gccgcccgca gcatgccgcg ggggcatat ccgagcgcct cgtgcatgcg       480
cacgctcggg tcgttgggca gcccgatgac agcgaccacg ctcttgaagc cctgtgcctc      540
cagggacttc agcaggtggg tgtagagcgt ggagcccagt cccgtccgct ggtggcgggg      600
ggagacgtac acgtcgact cggccgtcca gtcgtaggcg ttgcgtgcct tccaggggcc       660
cgcgtaggcg atgccggcga cctcgccgtc cacctcggcg acgagccagg gatagcgctc      720
ccgcagacgg acgaggtcgt ccgtccactc ctgcggttcc tgcggctcgg tacggaagtt      780
gaccgtgctt gtctcgatgt agtggttgac gatggtgcag accgccggca tgtccgcctc      840
ggtggcacgg cggatgtcgg ccgggcgtcg ttctgggtcc attgttcttc tttactctttt     900 gtgtgactga ggtttggtct agtgcttttgg tcatctatat ataatgataa caacaatgag    960
aacaagcttt ggagtgatcg gagggtctag gatacatgag attcaagtgg actaggatct     1020
acaccgttgg attttgagtg tggatatgtg tgaggttaat tttacttggt aacggccaca     1080
aaggcctaag gagaggtgtt gagacccta tcggcttgaa ccgctggaat aatgccacgt      1140
ggaagataat tccatgaatc ttatcgttat ctatgagtga aattgtgtga tggtggagtg     1200
gtgcttgctc attttacttg cctggtggac ttggccctttt ccttatgggg aatttatatt    1260
ttacttacta tagagctttc ataccttttt tttaccttgg atttagttaa tatataatgg     1320
tatgattcat gaataaaaat gggaaatttt tgaatttgta ctgctaaatg cataagatta     1380
ggtgaaactg tggaatatat atttttttca tttaaaagca aaatttgcct tttactagaa     1440
ttataaatat agaaaaatat ataacattca aataaaaatg aaaataagaa ctttcaaaaa     1500
acagaactat gtttaatgtg taaagattag tcgcacatca agtcatctgt tacaatatgt     1560
tacaacaagt cataagccca acaaagttag cacgtctaaa taaactaaag agtccacgaa     1620
aatattacaa atcataagcc caacaaagtt attgatcaaa aaaaaaaaac gcccaacaaa     1680
gctaaacaaa gtccaaaaaa aacttctcaa gtctccatct tcctttatga acattgaaaa     1740
ctatacacaa aacaagtcag ataaatctct ttctgggcct gtcttcccaa cctcctacat     1800
cacttcccta tcggattgaa tgttttactt gtaccttttc cgttgcaatg atattgatag     1860
tatgtttgtg aaaactaata gggttaacaa tcgaagtcat ggaatatgga tttggtccaa     1920
gattttccga gagctttcta gtagaaagcc catcaccaga aatttactag taaaataaat     1980
caccaattag gtttcttatt atgtgccaaa ttcaatataa ttatagagga tatttcaaat     2040
gaaaacgtat gaatgttatt agtaaatggt caggtaagac attaaaaaaa tcctacgtca     2100
gatattcaac tttaaaaatt cgatcagtgt ggaattgtac aaaaatttgg gatctactat     2160
atatatataa tgcttacaa cacttggatt ttttttgga ggctggaatt tttaatctac        2220
atatttgttt tggccatgca ccaactcatt gtttagtgta atactttgat tttgtcaaat     2280
atatgtgttc gtgtatattt gtataagaat tctttgacc atatacacac acacatatat       2340
atatatatat atatattata tatcatgcac ttttaattga aaaataata tatatatata      2400 tagtgcattt tttctaacaa ccatatatgt tgcgattgat ctgcaaaaat actgctagag     2460
```

```
taatgaaaaa tataatctat tgctgaaatt atctcagatg ttaagatttt cttaaagtaa    2520
attctttcaa attttagcta aaagtcttgt aataactaaa gaataataca caatctcgac    2580
cacggaaaaa aaacacataa taaatttgaa tttcgaccgc ggtacccgga attcgagctc    2640
ggtacccggg gatcttcccg atctagtaac atagatgaca ccgcgcgcga taatttatcc    2700
tagtttgcgc gctatatttt gttttctatc gcgtattaaa tgtataattg cgggactcta    2760
atcataaaaa cccatctcat aaataacgtc atgcattaca tgttaattat tacatgctta    2820
acgtaattca acagaaatta tatgataatc atcgcaagac cggcaacagg attcaatctt    2880
aagaaacttt attgccaaat gtttgaacga tctgcttcgg atcctctaga ccaagcttgc    2940
gggtttgtgt ttccatattg ttcatctccc attgatcgta ttaagaaagt atgatggtga    3000
tgtcgcagcc ttccgctttc gcttcacgga aaacctgaag cacactctcg gcgccatttt    3060
cagtcagctg cttgctttgt tcaaactgcc tccattccaa aacgagcggg tactccaccc    3120
atccggtcag acaatcccat aaagcgtcca ggttttcacc gtagtattcc ggaagggcaa    3180
gctccttttt caatgtctgg tggaggtcgc tgatacttct gatttgttcc ccgttaatga    3240 ctgcttttt catcggtagc taattttcttt aagtaaaaac tttgatttga gtgatgatgt    3300
tgtactgtta cacttgcacc acaagggcat atatagagca caagacatac acaacaactt    3360
gcaaaactaa cttttgttgg agcatttcga ggaaaatggg gagtagcagg ctaatctgag    3420
ggtaacatta aggtttcatg tattaatttg ttgcaaacat ggacttagtg tgaggaaaaa    3480
gtaccaaaat tttgtctcac cctgatttca gttatggaaa ttacattatg aagctgtgct    3540
agagaagatg tttattctag tccagccacc caccttatgc aagtctgctt ttagcttgat    3600
tcaaaaactg atttaattta cattgctaaa tgtgcatact tcgagcctat gtcgctttaa    3660
ttcgagtagg atgtatatat tagtacataa aaaatcatgt ttgaatcatc tttcataaag    3720
tgacaagtca attgtccctt cttgtttggc actatattca atctgttaat gcaaattatc    3780
cagttatact tagctagata tccaattttg aataaaaata gctcttgatt agtaaaccgg    3840
atagtgacaa agtcacatat ccatcaaact tctggtgctc gtggctaagt tctgatcgac    3900
atggggttaa aatttaaatt gggacacata atagcctat ttgtgcaaat ctccccatcg    3960
aaaatgacag attgttacat ggaaaacaaa aagtcctctg atagaagtcg caaagtatca    4020
caattttcta tcgagagata gattgaaaga agtgcaggga agcggttaac tggaacataa    4080
cacaatgtct aaattaattg cattcgctaa ccaaaaagtg tattactctc tccggtccac    4140
aataagttat ttttttggccc ttttttatg gtccaaaata agtgagtttt ttagatttca    4200
aaaatgattt aattattttt ttactacagt gcccttggag taaatggtgt tggagtatgt    4260
gttagaaatg tttatgtgaa gaaatagtaa aggttaatat gatcaatttc attgctattt    4320
aatgttaaaa tgtgaatttc ttaatctgtg tgaaaacacc aaaaaatcac ttattgtgga    4380
ccggagaaag tatataaata tatatttgga agcgactaaa aataaacttt tctcatatta    4440
tacgaaccta aaaacagcat atggtagttt ctagggaatc taaatcacta aaattaataa    4500
aagaagcaac aagtatcaat acatatgatt tacaccgtca aacacgaaat tcgtaaaatat    4560 ttaatataat aaagaattaa tccaaatagc ctcccaccct atkacttaaa ctaaaaataa    4620
ccagcgaatg tatattatat gcataattta tatattaaat gtgtataatc atgtataatc    4680
aatgtataat ctatgtatat ggttagaaaa agtaaacaat taatatagcc ggctatttgt    4740
gtaaaaatcc ctaatataat cgcgacggat ccccgggaat tccggggaag cttagatcca    4800
```

```
tggagccatt tacaattgaa tatatcctgc cg                                  4832

<210> SEQ ID NO 10
<211> LENGTH: 5865
<212> TYPE: DNA
<213> ORGANISM: Artificial
<220> FEATURE:
<223> OTHER INFORMATION: T-DNA of plasmid pCO113

<400> SEQUENCE: 10
aattcaaacg gtatatatcc tgccagtact cggccgtcga actcggccgt cgagtacatg      60
gtcgataaga aaaggcaatt tgtagatgtt aattcccatc ttgaaagaaa tatagtttaa     120
atatttattg ataaaataac aagtcaggta ttatagtcca agcaaaaaca taaatttatt     180
gatgcaagtt taaattcaga aatatttcaa taactgatta tatcagctgg tacattgccg     240
tagatgaaag actgagtgcg atattatgtg taatacataa attgatgata tagctagctt     300
agctcatcgg gggatcctag aacgcgtgat ctcagatctc ggtgacgggc aggaccggac     360
ggggcggtac cggcaggctg aagtccagct gccagaaacc cacgtcatgc cagttcccgt     420
gcttgaagcc ggccgcccgc agcatgccgc gggggggcata tccgagcgcc tcgtgcatgc     480
gcacgctcgg gtcgttgggc agcccgatga cagcgaccac gctcttgaag ccctgtgcct     540
ccagggactt cagcaggtgg gtgtagagcg tggagcccag tcccgtccgc tggtggcggg     600
gggagacgta cacggtcgac tcggccgtcc agtcgtaggc gttgcgtgcc ttccaggggc     660
ccgcgtaggc gatgccggcg acctcgccgt ccacctcggc gacgagccag ggatagcgct     720
cccgcagacg gacgaggtcg tccgtccact cctgcggttc ctgcggctcg gtacggaagt     780
tgaccgtgct tgtctcgatg tagtggttga cgatggtgca gaccgccggc atgtccgcct     840
cggtggcacg gcggatgtcg gccgggcgtc gttctgggtc cattgttctt ctttactctt     900
tgtgtgactg aggtttggtc tagtgctttg gtcatctata tataatgata acaacaatga     960
gaacaagctt tggagtgatc ggagggtcta ggatacatga gattcaagtg gactaggatc    1020
tacaccgttg gattttgagt gtggatatgt gtgaggttaa ttttacttgg taacggccac    1080
aaaggcctaa ggagaggtgt tgagacccct atcggcttga accgctggaa taatgccacg    1140
tggaagataa ttccatgaat cttatcgtta tctatgagtg aaattgtgtg atggtggagt    1200
ggtgcttgct cattttactt gcctggtgga cttggccctt tccttatggg gaatttatat    1260
tttacttact atagagcttt catacctttt ttttaccttg gatttagtta atatataatg    1320
gtatgattca tgaataaaaa tgggaaattt ttgaatttgt actgctaaat gcataagatt    1380
aggtgaaact gtggaatata tatttttttc atttaaaagc aaaatttgcc ttttactaga    1440
attataaata tagaaaaata tataacattc aaataaaaat gaaaataaga actttcaaaa    1500
aacagaacta tgtttaatgt gtaaagatta gtcgcacatc aagtcatctg ttacaatatg    1560
ttacaacaag tcataagccc aacaaagtta gcacgtctaa ataaactaaa gagtccacga    1620
aaatattaca aatcataagc ccaacaaagt tattgatcaa aaaaaaaaaa cgcccaacaa    1680
agctaaacaa agtccaaaaa aaacttctca agtctccatc ttcctttatg aacattgaaa    1740
actatacaca aaacaagtca gataaatctc tttctgggcc tgtcttccca acctcctaca    1800
tcacttccct atcggattga atgttttact tgtacctttt ccgttgcaat gatattgata    1860
gtatgtttgt gaaaactaat agggttaaca atcgaagtca tggaatatgg atttggtcca    1920
agattttccg agagctttct agtagaaagc ccatcaccag aaatttacta gtaaaataaa    1980
tcaccaatta ggtttcttat tatgtgccaa attcaatata attatagagg atatttcaaa    2040
```

-continued

```
tgaaaacgta tgaatgttat tagtaaatgg tcaggtaaga cattaaaaaa atcctacgtc    2100
agatattcaa ctttaaaaat tcgatcagtg tggaattgta caaaaatttg ggatctacta    2160
tatatatata atgctttaca acacttggat ttttttttgg aggctggaat ttttaatcta    2220
catatttgtt ttggccatgc accaactcat tgtttagtgt aatactttga ttttgtcaaa    2280
tatatgtgtt cgtgtatatt tgtataagaa tttctttgac catatacaca cacacatata    2340
tatatatata tatatattat atatcatgca cttttaattg aaaaaataat atatatatat    2400
atagtgcatt ttttctaaca accatatatg ttgcgattga tctgcaaaaa tactgctaga    2460
gtaatgaaaa atataatcta ttgctgaaat tatctcagat gttaagattt tcttaaagta    2520
aattctttca aattttagct aaaagtcttg taataactaa agaataatac acaatctcga    2580
ccacggaaaa aaaacacata ataaatttga atttcgaccg cggtacccgg aattcgagct    2640
cggtacccgg ggatcttccc gatctagtaa catagatgac accgcgcgcg ataatttatc    2700
ctagtttgcg cgctatattt tgttttctat cgcgtattaa atgtataatt gcgggactct    2760
aatcataaaa acccatctca taaataacgt catgcattac atgttaatta ttacatgctt    2820
aacgtaattc aacagaaatt atatgataat catcgcaaga ccggcaacag gattcaatct    2880
taagaaactt tattgccaaa tgtttgaacg atctgcttcg gatcctctag agccggaaag    2940
tgaaattgac cgatcagagt ttgaagaaaa atttattaca cactttatgt aaagctgaaa    3000
aaaacggcct ccgcaggaag ccgttttttt cgttatctga tttttgtaaa ggtctgataa    3060
tggtccgttg ttttgtaaat cagccagtcg cttgagtaaa gaatccggtc tgaatttctg    3120
aagcctgatg tatagttaat atccgcttca cgccatgttc gtccgctttt gcccgggagt    3180
ttgccttccc tgtttgagaa gatgtctccg ccgatgcttt tccccggagc gacgtctgca    3240
aggttccctt ttgatgccac ccagccgagg gcttgtgctt ctgattttgt aatgtaatta    3300
tcaggtagct tatgatatgt ctgaagataa tccgcaaccc cgtcaaacgt gttgataacc    3360
ggtaccatgg tagctaattt cttttaagtaa aaactttgat ttgagtgatg atgttgtact    3420
gttacacttg caccacaagg gcatatatag agcacaagac atacacaaca acttgcaaaa    3480
ctaacttttg ttggagcatt tcgaggaaaa tggggagtag caggctaatc tgagggtaac    3540
attaaggttt catgtattaa tttgttgcaa acatggactt agtgtgagga aaaagtacca    3600
aaattttgtc tcaccctgat ttcagttatg gaaattacat tatgaagctg tgctagagaa    3660
gatgtttatt ctagtccagc cacccacctt atgcaagtct gcttttagct tgattcaaaa    3720
actgatttaa tttacattgc taaatgtgca tacttcgagc ctatgtcgct ttaattcgag    3780
taggatgtat atattagtac ataaaaaatc atgtttgaat catctttcat aaagtgacaa    3840
gtcaattgtc ccttccttgtt tggcactata ttcaatctgt taatgcaaat tatccagtta    3900
tacttagcta gatatccaat tttgaataaa aatagctctt gattagtaaa ccggatagtg    3960
acaaagtcac atatccatca aacttctggt gctcgtggct aagttctgat cgacatgggg    4020
ttaaaattta aattgggaca cataaatagc ctatttgtgc aaatctcccc atcgaaaatg    4080
acagattgtt acatggaaaa caaaaagtcc tctgatagaa gtcgcaaagt atcacaattt    4140
tctatcgaga gatagattga aagaagtgca gggaagcggt taactggaac ataacacaat    4200
gtctaaatta attgcattcg ctaaccaaaa agtgtattac tctctccggt ccacaataag    4260 ttatttttg gccctttttt tatggtccaa aataagtgag ttttttagat ttcaaaaatg    4320
atttaattat ttttttacta cagtgcccctt ggagtaaatg tgttggagt atgtgttaga    4380
```

```
aatgtttatg tgaagaaata gtaaaggtta atatgatcaa tttcattgct atttaatgtt    4440
aaaatgtgaa tttcttaatc tgtgtgaaaa caaccaaaaa atcacttatt gtggaccgga    4500
gaaagtatat aaatatatat ttggaagcga ctaaaaataa acttttctca tattatacga    4560
acctaaaaac agcatatggt agtttctagg gaatctaaat cactaaaatt aataaaagaa    4620
gcaacaagta tcaatacata tgatttacac cgtcaaacac gaaattcgta aatatttaat    4680
ataataaaga attaatccaa atagcctccc accctataac ttaaactaaa aataaccagc    4740
gaatgtatat tatatgcata atttatatat taaatgtgta taatcatgta taatcaatgt    4800
ataatctatg tatatggtta gaaaaagtaa acaattaata tagccggcta tttgtgtaaa    4860
aatccctaat ataatcgcga cggatccccg ggaattccgg ggaagcttag atccatgcag    4920
atctgatcat gagcggagaa ttaagggagt cacgttatga cccccgccga tgacgcggga    4980
caagccgttt tacgtttgga actgacagaa ccgcaacgat tgaaggagcc actcagccgc    5040
gggtttctgg agtttaatga gctaagcaca tacgtcagaa accattattg cgcgttcaaa    5100
agtcgcctaa ggtcactatc agctagcaaa tatttcttgt caaaaatgct ccactgacgt    5160
tccataaatt cccctcggta tccaattaga gtctcatatt cactctcaat ccaaaccatg    5220
aaaaaagcag tcattaacgg ggaacaaatc agaagtatca gcgacctcca ccagacattg    5280
aaaaaggagc ttgcccttcc ggaatactac ggtgaaaacc tggacgcttt atgggattgt    5340
ctgaccggat gggtggagta cccgctcgtt ttggaatgga ggcagtttga acaaagcaag    5400
cagctgactg aaaatggcgc cgagagtgtg cttcaggttt tccgtgaagc gaaagcggaa    5460
ggctgcgaca tcaccatcat actttcttaa tacgatcaat gggagatgaa caatatggaa    5520
acacaaaccc gcaagcttgg tctagaggat cccccgatga gctaagctag ctatatcatc    5580
aatttatgta ttacacataa tatcgcactc agtctttcat ctacggcaat gtaccagctg    5640
atataatcag ttattgaaat atttctgaat ttaaacttgc atcaataaat ttatgttttt    5700
gcttggacta taatacctga cttgttattt tatcaataaa tatttaaact atatttcttt    5760
caagatggga attaacatct acaaattgcc ttttcttatc gaccatgtac atcgagctct    5820
ccccagatct gcatggagcc atttacaatt gaatatatcc tgccg                   5865
```

HYBRID *BRASSICA* PLANTS AND METHODS FOR PRODUCING SAME

CROSS-REFERENCE TO RELATED APPLICATIONS

This application is a National Stage entry of International Application No. PCT/EP2014/057770, filed Apr. 16, 2014, which claims priority to European Patent Application No. 13164421.3, filed Apr. 19, 2013. The disclosures of the prior applications are hereby incorporated in their entirety by reference.

FIELD OF THE INVENTION

This invention concerns transgenic *Brassica* plants, plant material and seeds, particularly oilseed rape plants, characterized in that these plants harbor a combination of two specific transformation events, particularly by the presence of a male-sterility gene, at a specific location in the *Brassica* genome and a fertility-restoration gene at another specific location in the *Brassica* genome. The invention also concerns a pair of transgenic *Brassica* plants, particularly oilseed rape plants, which is particularly suited for the production of hybrid seed. More specifically, one of the plants is characterized by being male-sterile, due to the presence in its genome of a male-sterility gene, while the other is characterized by carrying a fertility-restorer gene, capable of preventing the activity of the male-sterility gene. The pair of *Brassica* plants of the invention combines the ability to form hybrid seed with optimal overall agronomic performance, genetic stability and adaptability to different genetic backgrounds.

BACKGROUND OF THE INVENTION

The phenotypic expression of a transgene in a plant is determined both by the structure of the gene itself and by its location in the plant genome. At the same time the presence of the transgene (in a foreign DNA) at different locations in the genome will influence the overall phenotype of the plant in different ways. The agronomically or industrially successful introduction of a commercially interesting trait in a plant by genetic manipulation can be a lengthy procedure dependent on different factors. The actual transformation and regeneration of genetically transformed plants are only the first in a series of selection steps which include extensive genetic characterization, breeding, and evaluation in field trials.

The term "rapeseed" covers every seed of the *Brassica* species. *Brassica* is cultivated from China and India to Finland and Canada as one of the most valuable oil crops. Most *Brassica* types belong to the family of Cruciferae. They originated as a diploid species having aneuploid chromosome numbers ranging from 7 (*Brassica fruticulosa*) to 12 (*Sinapsis alba*). The most extensively grown *Brassica* species in Canada is known as turnip rape, or *Brassica campestris* (aa, n=10). *Brassica oleracea* (cc, n=9) has diversified in recent evolutionary history into at least six major horticultural types, including broccoli, cauliflower and cabbage. *Brassica nigra* (bb, n=8) or black mustard is a less important crop commercially and is mainly known for its seeds from which mustard was originally made. From these basic types, amphiploid hybrids have been derived in more recent evolutionary stages by intercrossing. The most important of these are *Brassica napus* (aacc), of which the winter types provide the highest rapeseed yields in northern Europe and *Brassica juncea* (aabb) or brown mustard which is one of the major oil crops of the Indian sub-continent. Though intercrossing between different *Brassica* species (particularly those with compatible genomes) is possible and often done for breeding purposes, not all traits (or genes) will be able to be transferred from one species to the other or, when transferred to a different species, will retain identical characteristics (or expression patterns). Thus, a genetic locus conferring optimal expression of a natural or chimeric gene in one *Brassica* species, will not necessarily have the same effect in another.

*Brassica* species are bisexual and typically 60-70% self pollinated. The production of hybrids and introduction of genetic variation as a basis for selection was traditionally dependent on the adaptation of natural occurring phenomena such as self-incompatibility and cytoplasmic male-sterility. Artificial pollination control methods such as manual emasculation or the use of gametocides are not widely applied in *Brassica* breeding due to their limited practicability and high cost respectively.

Transgenic methods have been developed for the production of male or female-sterile plants, which provide interesting alternatives to the traditional techniques.

EP 0,344,029 describes a system for obtaining nuclear male-sterility whereby plants are transformed with a male-sterility gene, which comprises for example a DNA encoding a barnase molecule under the control of a tapetum specific promoter TA29, which when incorporated into a plant ensures selective destruction of tapetum cells. Transformation of tobacco and oilseed rape plants with such a gene resulted in plants in which pollen formation was completely prevented (Mariani et al. 1990, Nature 347: 737-741).

Cytochemical and histochemical analysis of anther development of *Brassica napus* plants comprising the chimeric PTA29:barnase gene is described by De Block and De Brouwer (1993, Planta 189:218-225).

To restore fertility in the progeny of a male-sterile plant, a system was developed whereby the male-sterile plant is crossed with a transgenic plant carrying a fertility-restorer gene, which when expressed is capable of inhibiting or preventing the activity of the male-sterility gene (U.S. Pat. No. 5,689,041; U.S. Pat. No. 5,792,929; De Block and De Brouwer, supra). The use of coregulating genes in the production of male-sterile plants to increase the frequency of transformants having good agronomical performance is described in WO 96/26283. Typically, when the sterility DNA encodes a barnase, the coregulating DNA will encode a barstar.

Elite Event MS-B2, and male-sterile plants comprising this elite event conferring male-sterility have been extensively described in WO01/31042 (herein incorporated by reference) including characterization of the transgene and of the plant DNA sequences immediately flanking the inserted transgene.

Reference seed comprising elite event MS-B2 was deposited at the ATCC (10801 University Blvd., Manassas, Va. 20110-2209) on Oct. 14, 1999, under ATCC accession number PTA-850. Another sample of the same seed was deposited under accession number PTA-2485. An alternative name for MS-B2 is MS 11.

Elite Event RF-BN1, and plants comprising this elite event conferring male-sterility have been extensively described in WO01/41558 (herein incorporated by reference) including characterization of the transgene and of the plant DNA sequences immediately flanking the inserted transgene.

Reference seed comprising elite event RF-BN1 was deposited at the ATCC (10801 University Blvd., Manassas, Va. 20110-2209) on Sep. 20, 1999, under ATCC accession number PTA-730. An alternative name for RF-BN1 is Rf3.

WO01/41558 also describes elite event MS-BN1, male sterile plants comprising the event, as well as methods to identify such plants and progeny thereof. An alternative name for MS-BN1 is MS 8.

MS-BN1 and RF-BN1 events are comprised in hybrid *B. napus* plants sold under the brand name In Vigor® Canola.

These documents mentioned before do not describe the particular combination MS-B2 and RF-BN1 in *Brassica* plants nor the use thereof in hybrid seed production. RF-BN1 in *Brassica juncea* is also hitherto undescribed, as well as the use of MS-B2 to increase the yield in *Brassica* oilseed plants.

SUMMARY OF THE INVENTION

In one embodiment, the invention provides a method for producing hybrid seed from oilseed rape plants, such as *Brassica napus* or *Brassica juncea* comprising the steps of providing a male-sterile female parent oilseed rape plant comprising elite event MS-B2, reference seed comprising said elite event being deposited at the ATCC under deposit number ATCC_PTA 2485 or ATCC_PTA-850; providing a male-fertile male parent oilseed rape plant comprising elite event RF-BN1, preferably in homozygous form, reference seed comprising said elite event being deposited at the ATCC under deposit number ATCC_PTA-730; allowing pollen from said male parent oilseed rape plant to pollinate said female parent oilseed rape plant; and harvesting hybrid seed from said female parent plant.

In another embodiment, the invention provides an oilseed rape plant, such as *Brassica napus* or *Brassica juncea* plant, comprising in its nuclear genome at least one copy of elite event elite event MS-B2, reference seed comprising said elite event being deposited at the ATCC under deposit number ATCC_PTA 2485 or ATCC_PTA-850 and at least one copy of elite event RF-BN1, reference seed comprising said elite event being deposited at the ATCC under deposit number ATCC_PTA-730. Also provided are cells or tissues or seeds of such oilseed rape plants.

In yet another embodiment of the invention, a pair of oilseed rape plants is provided for use in production of hybrid seed wherein one of the oilseed rape plants comprises elite event MS-B2, reference seed comprising said elite event being deposited at the ATCC under deposit number ATCC_PTA 2485 or ATCC_PTA-850 and the other of said oilseed rape plants comprises elite event RF-BN1, reference seed comprising said elite event being deposited at the ATCC under deposit number ATCC_PTA-730.

It is also an object of the invention to provide genomic DNA of an oilseed rape plant, such as *Brassica napus* or *Brassica juncea* plant, comprising in its nuclear genome at least one copy of elite event elite event MS-B2, reference seed comprising said elite event being deposited at the ATCC under deposit number ATCC_PTA 2485 or ATCC_PTA-850 and at least one copy of elite event RF-BN1, reference seed comprising said elite event being deposited at the ATCC under deposit number ATCC_PTA-730.

Also provided by the invention are *Brassica juncea*, as well as cells and seeds thereof comprising elite event RF-BN1, reference seed comprising said elite event being deposited at the ATCC under deposit number ATCC_PTA-730. Such plants may further comprise elite event MS-B2, reference seed comprising said elite event being deposited at the ATCC under deposit number ATCC_PTA 2485 or ATCC_PTA-850.

The invention further provides use of elite event MS-B2, reference seed comprising said elite event being deposited at the ATCC under deposit number ATCC_PTA 2485 or ATCC_PTA-850 to increase seed yield in a transgenic oilseed rape plant such as a *Brassica juncea* plant.

In yet another embodiment of the invention, a method is provided to increase yield in oilseed rape plants comprising the step of providing the oilseed rape plant with elite event MS-B2, reference seed comprising said elite event being deposited at the ATCC under deposit number ATCC_PTA 2485 or ATCC_PTA-850.

DETAILED DESCRIPTION

Figure 1:
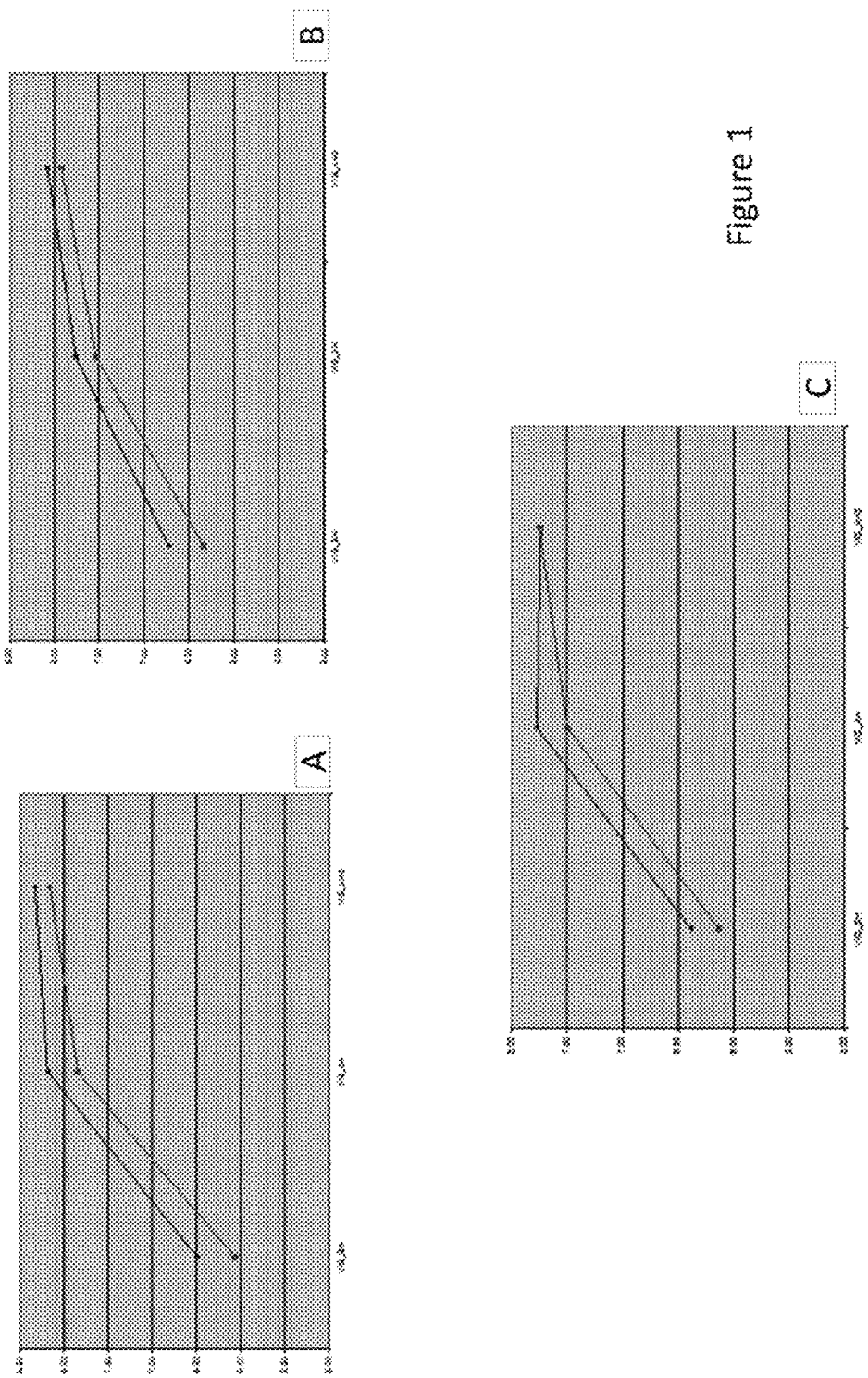
FIG. 1: Comparison of the vigor after herbicide application of MS/RF hybrid *B. napus* lines. Panel A: no glufosinate ammonium application. Panel B: one glufosinate ammonium application. Panel C: two glufosinate ammonium applications. Squares: MS-BN1/RF-BN1 plants; dots; MS-B2/RF-BN1 plants.

The current invention describes a novel combination of a male sterility event MS-B2 and a fertility restoration event RF-BN1 in oilseed rape plants, particularly *Brassica napus* and *Brassica juncea*.

The current invention is based inter alia on the unexpected finding that elite event RF-BN1 conferring fertility restoration is effective enough in *Brassica* oilseed rape plants to restore fertility when the plant further also contains elite event MS-B2 conferring male-sterility. Although RF-BN1 has previously successfully been used to restore fertility in oilseed rape plants, comprising elite event MS-BN1, it was unpredictable whether RF-BN1 could also been used to restore fertility in oilseed rape plants comprising elite event MS-B2. Different male-sterility comprising elite events have different expression levels of the barnase product expressed by the transgenic male-sterility gene and it cannot be predicted that the levels of barnase inhibitor, barstar, produced by transgenic fertility-restoration gene in RF-BN1 would match the expression of the barnase in other individual male-sterility events. As indicated in the examples below the combination of the current invention resulted in intrinsically higher yields that combination of the same male-sterility event MS-B2 with other fertility restoration events.

Furthermore, RF-BN1 has been previously described to be located on the C-genome (see WO 01/31042). Accordingly, the introduction of RF-BN1 from *B. napus* (aacc) into *B. juncea* (aabb) which does not contain a C-genome would not be considered straightforward by the skilled artisan. The current specification provides data that RF-BN1 is however located on the A-genome, allowing introduction in *B. juncea* by crossing.

In addition, field trials have uncovered that the presence of MS-B2 increases the average yield (grain yield) when compared to an isogenic plant line not containing MS-B2.

In one embodiment of the invention, a method is thus provided to produce hybrid seed from oilseed rape plants, such as *Brassica napus* or *Brassica juncea*, comprising the steps of provide a male-sterile female parent oilseed rape plant comprising elite event MS-B2 comprising a male sterility gene;

providing a male-fertile male parent oilseed rape plant comprising elite event RF-BN1 comprising a fertility restoration gene, preferably in homozygous form;

allowing pollen from the male parent oilseed rape plant to pollinate the female parent oilseed rape plant; and harvesting hybrid seed from the female parent plant.

The term "gene" as used herein refers to any DNA sequence comprising several operably linked DNA fragments such as a promoter and a 5' untranslated region (the 5'UTR), which together form the promoter region, a coding region (which may or may not code for a protein), and an untranslated 3' region (3'UTR) comprising a polyadenylation site. Typically in plant cells, the 5'UTR, the coding region and the 3'UTR are transcribed into a RNA which, in the case of a protein encoding gene, is translated into the protein. A gene may include additional DNA fragments such as, for example, introns. As used herein, a genetic locus is the position of a given gene in the genome of a plant.

The term "chimeric" when referring to a gene or DNA sequence is used to indicate that the gene or DNA sequence comprises at least two functionally relevant DNA fragments (such as promoter, 5'UTR, coding region, 3'UTR, intron) that are not naturally associated with each other and originate, for example, from different sources. "Foreign" referring to a gene or a DNA sequence with respect to a plant species is used to indicate that the gene or DNA sequence is not naturally found in that plant species, or is not naturally found in that genetic locus in that plant species. The term "foreign DNA" will be used herein to refer to a DNA sequence as it has incorporated into the genome of a plant as a result of transformation. The "transforming DNA" as used herein refers to a recombinant DNA molecule used for transformation. The transforming DNA usually comprises at least one "gene of interest" (e.g. a chimeric gene) which is capable of conferring one or more specific characteristics to the transformed plant. The term "recombinant DNA molecule" is used to exemplify and thus can include an isolated nucleic acid molecule which can be DNA and which can be obtained through recombinant or other procedures.

As used herein the term "transgene" refers to a gene of interest as incorporated in the genome of a plant. A "transgenic plant" refers to a plant comprising at least one transgene in the genome of all of its cells.

The foreign DNA present in the plants of the present invention will preferably comprise two genes of interest, more specifically, either a male-sterility gene and a herbicide resistance gene or a fertility restorer gene and a herbicide resistance gene.

A "male-sterility gene" as used herein refers to a gene which upon expression in the plant renders the plant incapable of producing fertile, viable pollen. An example of a male sterility gene is a gene comprising a DNA sequence encoding barnase, under the control of a promoter directing expression in tapetum cells. More specifically, according to the present invention the male-sterility gene is "TA29-barnase" as described herein.

A "fertility restorer gene" as used herein refers to a gene which upon expression in a plant comprising a male-sterility gene, is capable of preventing phenotypic expression of the male-sterility gene, restoring fertility in the plant. More specifically the fertility restorer gene will comprise a DNA encoding a protein or polypeptide capable of preventing phenotypic expression of the male-sterility gene, under the control of a promoter directing expression in at least the cells in which the male-sterility DNA is expressed. More specifically, according to the present invention, the fertility restorer gene is "TA29-barstar" as described herein.

The incorporation of a recombinant DNA molecule in the plant genome typically results from transformation of a cell or tissue (or from another genetic manipulation). The particular site of incorporation is either due to chance or is at a predetermined location (if a process of targeted integration is used).

The foreign DNA can be characterized by the location and the configuration at the site of incorporation of the recombinant DNA molecule in the plant genome. The site in the plant genome where a recombinant DNA has been inserted is also referred to as the "insertion site" or "target site". Insertion of the transgene into the plant genome can be associated with a deletion of plant DNA, referred to as "target site deletion". A "flanking region" or "flanking sequence" as used herein refers to a sequence of at least 20 bp, preferably at least 50 bp, and up to 5000 bp of the plant genome which is located either immediately upstream of and contiguous with or immediately downstream of and contiguous with the foreign DNA. Transformation procedures leading to random integration of the foreign DNA will result in transformants with different flanking regions, which are characteristic and unique for each transformant. When the transgene is introduced into a plant through traditional crossing, its insertion site in the plant genome, or its flanking regions will generally not be changed. An "insertion region" as used herein refers to the region corresponding to the region of at least 40 bp, preferably at least 100 bp, and up to more than 10000 bp, encompassed by the upstream and the downstream flanking regions of a transgene in the (untransformed) plant genome and including the insertion site (and possible target site deletion). Taking into consideration minor differences due to mutations within a species, an insertion region will retain at least 85%, preferably 90%, more preferably 95%, and most preferably 100% sequence identity with the sequence comprising the upstream and downstream flanking regions of the foreign DNA in a given plant of that species.

Expression of a gene of interest refers to the fact that the gene confers on the plant one or more phenotypic traits (e.g. herbicide tolerance) that were intended to be conferred by the introduction of the recombinant DNA molecule—the transforming DNA—used during transformation (on the basis of the structure and function of part or all of the gene(s) of interest).

An "event" is defined as a (artificial) genetic locus that, as a result of genetic manipulation, carries a foreign DNA comprising at least one copy of the gene(s) of interest. The typical allelic states of an event are the presence or absence of the foreign DNA. As used herein an "MS" event and an "RF" event will refer to events carrying the "TA29-barnase" and "TA29-barstar" transgenes respectively. An event is characterized phenotypically by the expression of one or more transgenes. At the genetic level, an event is part of the genetic makeup of a plant. At the molecular level, an event is characterized by the restriction map (e.g. as determined by Southern blotting) and/or by the upstream and/or downstream flanking sequences of the transgene, and/or the molecular configuration of the transgene. Usually transformation of a plant with a transforming DNA comprising at least one gene of interest leads to a multitude of events, each of which is unique.

An "elite event", as used herein, is an event which is selected from a group of events, obtained by transformation with the same transforming DNA or by back-crossing with plants obtained by such transformation, based on the expression and stability of the transgene and its compatibility with optimal agronomic characteristics of the plant comprising it. Thus the criteria for elite event selection are one or more, preferably two or more, advantageously all of the following:
a) That the presence of the transgene does not compromise other desired characteristics of the plant, such as those relating to agronomic performance or commercial value:
b) That the event is characterized by a well defined molecular configuration which is stably inherited and for which appropriate diagnostic tools for identity control can be developed;
c) That the gene(s) of interest in the transgene show(s) a correct, appropriate and stable spatial and temporal phenotypic expression, both in heterozygous (or hemizygous) and homozygous condition of the event, at a commercially acceptable level in a range of environmental conditions in which the plants carrying the event are likely to be exposed in normal agronomic use.

It is preferred that the foreign DNA is associated with a position in the plant genome that allows introgression into desired commercial genetic backgrounds.

The status of an event as an elite event is confirmed by introgression of the elite event in different relevant genetic backgrounds and observing compliance with one, two or all of the criteria e.g. a), b) and c) above.

Additionally, for the transgenes encoding male sterility and fertility restoration described herein, selection of the elite events will also be determined on the compatibility between these events, more specifically that the progeny resulting from a cross between a plant carrying a male-sterility event and a plant carrying a fertility restorer event, in which both events are present have the following characteristics:
a) adequate phenotypic expression of the fertility restored phenotype, i.e. male fertility; and
b) phenotypic expression at a commercially acceptable level in a range of environmental conditions in which plants carrying the two events are likely to be exposed in normal agronomic use.

An "elite event" thus refers to a genetic locus comprising a transgene, which answers to the above-described criteria. A plant, plant material or progeny such as seeds can comprise one or more elite events in its genome.

Elite event MS-B2 has been characterized extensively as described in WO 01/31042 (see particularly examples 1 and 3). The transforming DNA has been described in Example 1. The flanking plant DNA sequences after transgene insertion have been isolated and identified (see WO 01/31042, particularly examples 3.2 as well as SEQ ID Nos 1 and 2). A diagnostic PCR allowing identification of elite event MS-B2 in biological material has also been described in WO 01/31042, particularly Example 5. When elite event MS-B2 is present in *Brassica* plants, cells, seed or tissues, genomic DNA thereof can be used to amply a DNA fragment of between 160 and 200 bp, particularly about 183 bp, using a polymerase chain reaction with two primers having the nucleotide sequence of SEQ ID No 3 and SEQ ID No. 4 respectively. Reference seed has been deposited at the ATCC under deposit number ATCC_PTA-850 or PTA-2485. An alternative names for Elite event MS-B2 is MS11.

Elite event RF-BN1 has been characterized extensively as described in WO 01/41558 (sec particularly examples 1b and 4.2.2). The transforming DNA has been described in Example 1b. The flanking plant DNA sequences after transgene insertion have been isolated and identified (see WO 01/31042, particularly examples 4.2.2 as well as SEQ ID Nos 5 and 6). A diagnostic PCR allowing identification of elite event RF-BN1 in biological material has also been described in WO 01/41558, particularly Example 5.2. When elite event RF-BN1 is present in *Brassica* plants, cells, seed or tissues, genomic DNA thereof can be used to amply a DNA fragment of between 195 and 235 bp, particularly about 215 bp, using a polymerase chain reaction with two primers having the nucleotide sequence of SEQ ID No 7 and SEQ ID No. 8 respectively. Reference seed has been deposited at the ATCC under deposit number ATCC_PTA-730. Alternative names for RF-BN1 are RF3 or ACS-BN003-6.

Plants harboring RF-BN1 or MS-B2 can, for example, be obtained from the seeds deposited at the ATCC. Such plants can be further propagated and/or used in a conventional breeding scheme to introduce the elite event of the invention into other cultivars of the same plant species. The deposited seeds belong to the species *Brassica napus*. Nevertheless, methods to introduce alleles or transgenes located on the A-genome from *B. napus* to *B. juncea* are well known in the art and include repeated back-crossing.

The invention provides for the first time *B. juncea* plants, seeds, cells and tissues comprising in their nuclear genome elite event RF-BN1, comprising a fertility restoration genome. Previously available information indicated that the elite event RF-BN1 was present on the C-genome: however information provided herein located RF-BN1 insertion in the A-genome allowing transfer of the elite event to *B. juncea*.

*Brassica* plants harboring MS-B2 and/or RF-BN1 are also characterized by their glufosinate tolerance, which in the context of the present invention includes that plants are tolerant to the herbicide Liberty™. Tolerance to Liberty™ is defined by the criterium that spraying of the plants in the three to four leaf stage (3V to 4V) with at least 200 grams active ingredient/hectare (g.a.i./ha), preferably 400 g.a.i./ha, and possibly up to 1600 g.a.i./ha does not kill the plants. Plants harboring MS-B2 and/or RF-BN1 can further be characterized by the presence in their cells of phosphinothricin acetyl transferase as determined by a PAT assay (De Block et al, 1987, EMBO J. 6: 2513-2518).

The *Brassica* plants of this invention can be cultivated in a conventional way. The presence of the 35S-bar gene ensures that they are tolerant to glufosinate. Therefore, weeds in the fields where such *Brassica* plants are grown can be controlled by application of herbicides comprising glufosinate as an active ingredient (such as Liberty™).

Field trials have further unveiled that the presence of MS-B2 in *Brassica* plants results in a seed or grain yield increase when compared to isogenic plant line without MS-B2. Accordingly, an embodiment of the current invention is a method to increase seed yield in oilseed rape plants comprising the step of providing the oilseed rape plant with elite MS-B2.

As used in the claims below, unless otherwise clearly indicated, the term "plant" is intended to encompass plant tissues, at any stage of maturity, as well as any cells, tissues, or organs taken from or derived from any such plant, including without limitation, any seeds, leaves, stems, flowers, roots, single cells, gametes, cell cultures, tissue cultures or protoplasts. Plant cells as used herein encompass non-regenerable plant cells.

"*Brassica*" plants as used herein refers to plants of the family of the Brassicacea, preferably plants comprising an A genome. Preferably the *Brassica* plant will belong to one of the species *Brassica napus, Brassica rapa* (or *campestris*), or *Brassica junea*. Alternatively, the plant can belong to a species originating from intercrossing of these *Brassica* species, such as *B. napocampestris*, or of an artificial crossing of one of these *Brassica* species with another species of the *Cruciferacea*. As used herein "oilseed plant" refers to any one of the species *Brassica napus, Brassica rapa* (or *campestris*), or *Brassica juncea*.

Oilseed plants according to the current invention can also be treated with herbicides including Clopyralid, Diclofop, Fluazifop, Glufosinate, Glyphosate, Metazachlor, Trifluralin Ethametsulfuron, Quinmerac, Quizalofop, Clethodim, Tepraloxydim; with fungicides, including Azoxystrobin, Carbendazim, Fludioxonil, Iprodione, Prochloraz, Vinclozolin or with insecticides, including Carbofuran, Organophosphates, Pyrethroids, Thiacloprid, Deltamethrin, Imidacloprid, Clothianidin, Thiamethoxam, Acetamiprid, Dinetofuran, β-Cyfluthrin, gamma and lambda Cyhalothrin, tau-Fluvaleriate, Ethiprole, Spinosad, Spinotoram, Flubendiamide, Rynaxypyr, Cyazypyr or 4-[[(6-Chlorpyridin-3-yl) methyl](2,2-difluorethyl)amino]furan-2(5H)-on.

As used herein "comprising" is to be interpreted as specifying the presence of the stated features, integers, steps or components as referred to, but does not preclude the presence or addition of one or more features, integers, steps or components, or groups thereof. Thus, e.g., a nucleic acid or protein comprising a sequence of nucleotides or amino acids, may comprise more nucleotides or amino acids than the actually cited ones, i.e., be embedded in a larger nucleic acid or protein. A chimeric gene comprising a DNA sequence which is functionally or structurally defined, may comprise additional DNA sequences, etc.

The following examples describe the characteristics of oilseed rape plants harboring the elite events MS-B2 and RF-BN1.

Unless otherwise stated, all recombinant DNA techniques are carried out according to standard protocols as described in Sambrook et al. (1989) *Molecular Cloning: A Laboratory Manual*, Second Edition, Cold Spring Harbour Laboratory Press, NY and in Volumes 1 and 2 of Ausubel et al. (1994) *Current Protocols in Molecular Biology*, Current Protocols, USA. Standard materials and methods for plant molecular work are described in Plant Molecular Biology Labfax (1993) by R. D. D. Croy published by BIOS Scientific Publications Ltd (UK) and Blackwell Scientific Publications. UK.

In the description and examples, reference is made to the following sequences:
SEQ ID No 1: 5' flanking sequence MS-B2
SEQ ID No 2: 3' flanking sequence MS-B2
SEQ ID No 3: oligonucleotide primer 1 for detection of MS-B2
SEQ ID No 4: oligonucleotide primer 2 for detection of MS-B2
SEQ ID No 5: 5' flanking sequence RF-BN1
SEQ ID No 6: 3' flanking sequence RF-BN1
SEQ ID No 7: oligonucleotide primer 1 for detection of RF-BN1
SEQ ID No 8: oligonucleotide primer 2 for detection of RF-BN1
SEQ ID No 9: plasmid pTHW118
SEQ ID No 10: plasmid pTCO113

The above description of the invention is intended to be illustrative and not limiting. Various changes or modifications in the embodiments described may occur to those skilled in the art. These can be made without departing from the spirit or scope of the invention.

EXAMPLES

Example 1. Short Description of MS-B2 and RF-BN1

1.1. Elite Event MS-B2

Elite event MS-B2 was generated as by *Agrobacterium*-mediated transformation of *B. napus* plants with a chimeric DNA comprising the barnase gene under the control of a tapetum specific promoter (pTCO113).

Plasmid pTCO113 was essentially derived from the intermediate vector pGSV1. Vector pGSV1 is itself derived from pGSC1700 (Cornelissen and Vandewielle, 1989), but comprises an artificial T-region consisting of the left and right border sequences of the TL-DNA form pTiB6S3 and multilinker cloning sites allowing the insertion of chimeric genes between the T-DNA border repeats. The pGSV1 vector is provided with a barstar gene on the plasmid mainframe, with regulatory signals for expression in *E. coli*.

A full description of the DNA comprised between the border repeats of pTCO113 is given in Table 1 (SEQ ID No. 10):

TABLE 1

| Nucleotide positions of the DNA comprised between the T-DNA border repeats of pTCO113 | | |
|---|---|---|
| Nt positions | Orientation | Description and references |
| 1-25 | | Right border repeat from the TL-DNA from pTiB6S3 (Gielen et al . . . (1984) The EMBO Journal 3: 835-846). |
| 26-53 | | Synthetic polylinker derived sequences |
| 54-90 | | Residual sequence from the TL-DNA at the right border repeat |
| 91-97 | | Synthetic polylinker derived sequences |

TABLE 1-continued

Nucelotide positions of the DNA comprised between the T-DNA border repeats of pTCO113

| Nt positions | Orientation | Description and references |
| --- | --- | --- |
| 309-98 | Counter clockwise | The 3'untranslated end from the TL-DNA gene 7 (3'g7) of pTiB66S3 (Velten and Schell, (1985) Nucleic Acids Research 13: 6981-6998; Dhaese et al . . . (1983) The EMBO Journal 3: 835-846). |
| 310-331 | | Synthetic polylinker derived sequences |
| 883-332 | Counter clockwise | The coding sequence of the bialaphos resistance gene (bar) of *Streptomyces hygroscopicus* (Thompson et al . . . (1987) The EMBO Journal 6: 2519-2523). The N-terminal two codons of the wild type bar coding region have been substituted for the codons ATG and GAC respectively. |
| 2609-884 | Counter clockwise | The promoter from the atS1A ribulose-1,5-biphosphate carboxylase small subunit gene from *Arabidopsis thaliana* (PssuAra) (Krebbers et al . . . (1988) Plant Molecular Biology 11: 745-759). |
| 2610-2659 | | Synthetic polylinker derived sequences |
| 2920-2660 | Counter clockwise | A 260 bp TaqI fragment from the 3'untranslated end of the nopaline synthase gene (3'nos) from the T-DNA of pTiT37 and containing plant polyadenlyation signals (Depicker et al . . . (1982) Journal of Molecular and Applied Genetics 1: 561-573). |
| 2921-2936 | | Synthetic polylinker derived sequences |
| 3032-2937 | | 3'untranslated region downstream from the barnase coding sequence of *B. amyloliquefaciens* |
| 3368-3033 | Counter clockwise | The coding region of the barnase gene from *Bacillus amyloliquefaciens* (Hartley (1988) Journal of Molecular Biology 202: 913-915). |
| 4878-3369 | Counter clockwise | The promoter region of the anther-specific gene TA29 from *Nicotiana tabacum*. The promoter comprises the 1.5 kb of the sequence upstream from the ATG initiation codon (Seurinck et al . . . , (1990) Nucleic Acids Research 18: 3403). |
| 4879-4924 | | Synthetic polylinker derived sequences |
| 4925-5215 | Clockwise | The promoter of the nopaline synthase gene from the T-DNA of pTiT37 of *Agrobacterium tumefaciens* (PNos). The nucleotide sequence of the PNos promoter is descibed by Depicker et al . . . , (1982) Journal of Molecular and Applied Genetic 1: 561-573. |
| 5216-5217 | | Synthetic polylinker derived sequences |
| 5218-5490 | Clockwise | The coding region of the barstar gene of *Bacillus amyloliquefaciens* (Hartley (1988) Journal of Molecular Biology 202: 913-915). |
| 5491-5530 | | Sequence from the 3'untranslated end of the barstar gene from *Bacillus amyloliquefaciens* |
| 5531-5554 | | Synthetic polylinker derived sequences |
| 5555-5766 | Clockwise | The 3'untranslated end from the TL-DNA gene 7 (3'g7) of pTiB6S3 (Velten and Schell. (1985) Nucleic Acids Research 13: 6981-6998; Dhaese et al . . . (1983) The EMBO Journal 3: 835-846). |
| 5767-5773 | | Synthetic polylinker derived sequence |
| 5774-5810 | | Residual sequences fom the TL-DNA at the right border repeat |
| 5811-5840 | | Synthetic polylinker derived sequence |
| 5841-5865 | | Left border repeat from the TL-DNA from pTiB6S3 (Gielen et al . . . (1984) The EMBO Journal 3: 835-846). |

The flanking sequences were isolated as described in WO 01/31042.

Right (5') Flanking, Region

The 5' flanking region was amplified as ca. 415 bp fragment, the complete sequence of which was determined (SEQ ID No. 1). The sequence between nucleotide 1 and 234 corresponds to plant DNA, while the sequence between nucleotide 235 and 415 corresponds to T-DNA.

Left (3') Flanking Region

The 3' flanking region was amplified as ca. 416 bp fragment, the complete sequence of which was determined (SEQ ID No. 2). The sequence between nucleotide 1 and 193 corresponds to T-DNA, while the sequence between nucleotide 194 and 416 corresponds to plant DNA.

PCR Identification of MS-B2

As described in WO 01/31042, MS-B2 comprising biological material can be identified using the therein described PCR identification protocol.

The following primers, which specifically recognize the foreign DNA and a flanking sequence of MS-B2 may be used:

```
B01:
                                          (SEQ ID No. 3)
5'-gAA.ATC.CAT.gTA.AAg.CAg.CAg.gg-3'
       (target: plant DNA)

B02:
                                          (SEQ ID No. 4)
5'-gCT.Tgg.ACT.ATA.ATA.CTT.gAC-3'
       (target: T-DNA)
```

The expected amplified fragments in the PCR reaction are:

for primer pair B01-B02: 183 bp (MS-B2 Elite Event)

1.2. Elite Event RF-BN1

Elite event RF-BN1 was generated as by *Agrobacterium*-mediated transformation of *B. napus* plants with a chimeric DNA comprising the barstar gene under the control of a TA29 promoter (pTHW118).

Plasmid pTHW118 was also essentially derived from the intermediate vector pGSV1 (described above). A full description of the DNA comprised between the border repeats of pTHW118 is given in Table 2 (SEQ ID No. 9):

TABLE 2

T-DNA of plasmid pTHW118

| nt positions | Orientation | Description and references |
| --- | --- | --- |
| 1-25 | | Right border repeat from the TL-DNA from pTiB6S3 (Gielen et al (1984) The EMBO Journal 3: 835-846). |
| 26-53 | | Synthetic polylinker derived sequences |
| 54-90 | | Residual sequence from the TL-DNA at the right border repeat. |
| 91-97 | | Synthetic polylinker derived sequences |
| 309-98 | Counter clockwise | The 3'untranslated end from the TL-DNA gene 7 (3'g7) of pTiB6S3 (Velten and Schell. (1985) Nucleic Acids Research 13: 6981-6998; Dhaese et al. (1983) The EMBO Journal 3: 835-846). |
| 310-330 | | Synthetic polylinker derived sequences |
| 883-331 | Counter clockwise | The coding sequence of the bialaphos resistance gene (bar) of *Streptomyces hygroscopicus* (Thompson et al. (1987) The EMBO Journal 6: 2519-2523). The N-terminal two codons of the wild type bar coding region have been substituted for the codons ATG and GAC respectively. |
| 2608-883 | Counter clockwise | The promoter from the atS1A ribulose-1,5-biphosphate carboxylase small subunit gene from *Arabidopsis thaliana* (PssuAra) (Krebbers et al. (1988) Plant Molecular Biology 11: 745-759). |
| 2609-2658 | | Synthetic polylinker derived sequences |
| 2919-2659 | Counter clockwise | A 260 bp TaqI fragment from the 3' untranslated end of the nopaline synthase gene (3'nos) from the T-DNA of pTiT37 and containing plant polyadenylation signals (Depicker et al. (1982) Journal of Molecular and Applied Genetics 1: 561-573). |
| 2920-2940 | | Synthetic polylinker derived sequences |
| 2941-2980 | | 3'untranslated region downstream from the barstar coding sequence from *Bacillus amyloliquefaciens* |
| 3253-2981 | Counter clockwise | The coding region of the barstar gene from *Bacillus amyloliquefaciens* (Hartley (1988) Journal of Molecular Biology 202: 913-915). |
| 4762-3254 | Counter clockwise | The promoter region of the anther-specific gene TA29 from *Nicotiana tabacum*. The promoter comprises the 1.5 kb of the sequence upstream from the ATG intitiation codon (Seurinck et al. (1990) Nucleic Acids Research 18: 3403). |
| 4763-4807 | | Synthetic polylinker derived sequences |
| 4808-4832 | | Left border repeat from the TL-DNA from pTiB6S3 (Gielen et al (1984) The EMBO Journal 3: 835-846). |

The flanking sequences were isolated as described in WO 01/41558.

Right (5') Flanking Region

The 5' flanking region was amplified as ca. 1077 bp fragment, the complete sequence of which was determined (SEQ ID No. 5). The sequence between nucleotide 1 and 881 corresponds to plant DNA, while the sequence between nucleotide 882 and 1077 corresponds to T-DNA.

Left (3') Flanking Region

The 3' flanking region was amplified as ca. 1500 bp fragment, the complete sequence of which was determined (SEQ ID No. 6). The sequence between nucleotide 1 and 166 corresponds to T-DNA, while the sequence between nucleotide 167 and 1441 corresponds to plant DNA.

PCR Identification of RF-BN1

As described in WO 01/41558, RF-BN1 comprising biological material can be identified using the therein described PCR identification protocol.

To identify plant material comprising RF-BN1, the following primers, which specifically recognize the transgene and a flanking sequence of RF-BN1 are used:

```
BNA03:
                                                  (SEQ ID 7)
5'-TCA.TCT.ACg.gCA.ATg.TAC.CAg-3'
    (target: transgene)

BNA04:
                                                  (SEQ ID 8)
5'-Tgg.ACC.CCT.Agg.TAA.ATg.CC-3'
    (target: plant DNA)
```

The expected amplified fragments in the PCR reaction are:

For primer pair BNA03-BNA04: 215 bp (RF-BN1 Elite Event)

Example 2. Identification of the Genome on which the RF-BN1 Locus is Located and Introduction into *Brassica juncea*

To determine whether the RF-BN1 locus is located on the A or C genome of *Brassica napus*, the co-heritage or linkage of RF-BN1 with known markers on the *Brassica* genome was analyzed in 4 different segregating *B. napus* BC1 populations derived from a cross between the donor line containing the RF-BN1 transgene in a homozygous state an a recurrent parent not containing the transgene. The AFLP method was used to generate genetic markers. AFLP analysis was adapted from Vos et al. (1995, NAR 23:4407-4414, EP0534858 and U.S. Pat. No. 6,045,994). In order to identify AFLP markers linked to RF-BN1, bulked segregant analysis (BSA) was carried out according to Michelmore et al. (1991, Proc. Natl. Acad. Sci. USA 88:9828-9823).

All the AFLP genetic markers that displayed differential amplification between the pools of RF-BN1 positive plants (containing a visible AFLP marker) and RF-BN1 negative plants (where the same marker was not visible) were analyzed on at least 46 individual samples of the BC1 population in which the AFLP marker has been shown to be potentially linked in the BSA analysis. Only markers that showed considerable amount of co-segregation with the RF-BN1 PCR marker where retained, potential other markers not satisfying this criterium were discarded as false positives from the BSA analysis. Linkage analysis was carried out using data from the retained AFLP markers and the RF-BN1 PCR marker data generated on single plants for each BC1 population separately using JoinMap Version 3.0 (Van Ooijen and Vorrips (2001) JoinMap Version 3.0, Software for the calculation of genetic linkage maps, Plant Research International, Wageningen, The Netherlands). As the 4 individual maps around the RF-BN1 locus showed considerable agreement, these 4 BC1 maps could be integrated into one BC1 map representing the region around the RF-BN1 locus using the same software, allowing local mapping of the RF-BN1 locus.

The resulting local map of the RF-BN1 region was then compared to a genetic reference map that represents all *B. napus* chromosomes. For this reference map, chromosome numbers had already been assigned according to Sharpe et al. (1995, Genome 38:112-1121) and Parkin et al. (1995, Genome 38:1122-1131). N01 to N10 are A-genome chromosomes, while N11 to N19 are C-genome chromosomes. A very clear correlation was found between the RF-BN1 region map and the N07 chromosome from the reference map, which is know to be an A-genome chromosome. RF-BN1 is positioned on the A-genome of *B. napus*.

Event RF-BN1 was introduced by repeated backcrossing from Drakkar variety plants comprising event RF-BN1 into a *Brassica juncea* cultivar. After at least 4 generations of accelerated backcrosses, the *B. juncea* plants were examined and it was established that:

a) the presence of the foreign DNA did not compromise other desired characteristics of the plant, such as those relating to agronomic performance or commercial value;

b) the event was characterized by a well defined molecular configuration which was stably inherited; and c) the gene(s) of interest in the foreign DNA showed a correct, appropriate and stable spatial and temporal phenotypic expression, both in heterozygous (or hemizygous) and homozygous condition of the event, at a commercially acceptable level in a range of environmental conditions in which the plants carrying the event are likely to be exposed in normal agronomic use. Furthermore, the plants were evaluated for their agronomical characteristics and performance as compared with wild-type *Brassica juncea* species.

Extensive testing in the field demonstrated that RF-BN1 in *Brassica juncea* resulted in plants which showed adequate expression of the genes of interest in the foreign DNA, i.e. a male-sterile phenotype, combined with optimal agronomic performance. Thus, although originally developed in a *B. napus*, it was surprisingly found that RF-BN1 was also an elite event in *Brassica juncea*. Moreover, RF-BN1 could be efficiently used to restore fertility in *B. juncea* plants comprising MS-B2.

Example 3. Agronomic Performance of MS-B2/RF-BN1 Plants

*Brassica* oilseed rape plants comprising MS-B2 RF-BN1 events were field tested, together with isogenic not transgenic control checks as well as MS-B2 plants comprising other restorer events. Relevant yield data are summarized in the tables below.

Note that field trial data for additional plant lines were included in the analysis for calculation of mean, significant etc.

It will be clear that plant lines comprising MS-B2 and RF-BN1 yield consistently higher than plant lines comprising MS-B2 and other male-restoration events such as RF-BN2.

It will further be clear that plant lines comprising MS-B2 yield higher than isogenic non-transgenic plant lines.

TABLE 3

Field trials at geographic location 1

| | Variable description | |
|---|---|---|
| Pedigree | YLD(9) kg Mean | YLD(9) kg % Checks |
| MS-B2 BC4 | 1458.95 | 102.31 |
| Isogenic line | 1529.45 | 107.26 |
| Isogenic line | 1552.57 | 108.88 |
| Isogenic line (75% seed density) | 1560.60 | 109.44 |
| Isogenic line (50% seed density) | 1560.93 | 109.46 |
| Isogenic line (50% seed density) | 1573.65 | 110.35 |
| Isogenic line (75% seed density) | 1581.22 | 110.89 |
| MS-B2 BC4 | 1886.26 | 132.28 |
| MS-B2 BC4 × RF-BN1 + accBC3 | 1468.76 | 103.00 |
| MS-B2 BC4 × RF-BN2 | 1013.52 | 71.08 |
| Ms11 BC4 × RF-BN1 + accBC3 | 1486.27 | 104.23 |
| Ms11 BC4 × RF-BN2 + BC4 | 1017.70 | 71.37 |
| Ms11 BC4 × RF-BN1 + accBC3 | 1522.29 | 106.75 |
| Ms11 BC4 × RF-BN2 + BC5 | 1183.72 | 83.01 |
| Ms11 BC4 × RF-BN1 + accBC3 | 1565.97 | 109.82 |
| Ms11 BC4 × RF-BN2 + BC5 | 1172.28 | 82.21 |
| Mean | 1403.99 | 98.46 |
| Check mean | 1425.99 | 100.00 |
| Signification | ** | ** |
| P.p.d.s. 5% | 362.98 | 25.45 |
| P.p.d.s. 1% | 479.76 | 33.64 |
| P.p.e.s. 5% | 486.84 | 34.14 |
| P.p.e.s. 1% | 548.55 | 38.47 |
| C.V. | 20.50% | 20.50% |
| Res. std. dev. | 289.36 | 20.29 |
| #reps analysed | 4 | 4 |

TABLE 4

Field trials at geographic location 2

| | Variable description | |
|---|---|---|
| Pedigree | YLD(9) kg Mean | YLD(9) kg % Checks |
| MS-B2 BC4 | 1573.12 | 93.52 |
| Isogenic line (50% seed density) | 1671.86 | 99.39 |
| Isogenic line (75% seed density) | 1689.03 | 100.41 |
| Isogenic line | 1692.71 | 100.63 |
| MS-B2 BC4 × RF-BN1 + accBC3 | 1776.16 | 105.59 |
| MS-B2 BC4 × RF-BN2 + BC4 | 1285.16 | 76.40 |
| MS-B2 BC4 × RF-BN1 + accBC3 | 1716.48 | 102.04 |
| MS-B2 BC4 × RF-BN2 + BC5 | 1255.13 | 74.61 |
| MS-B2 BC4 × RF-BN1 RF-BN1 BC5F2 | 1973.41 | 117.31 |
| Mean | 1586.57 | 94.32 |
| Check mean | 1682.17 | 100.00 |
| Signification | ** | ** |
| P.p.d.s. 5% | 186.23 | 11.07 |
| P.p.d.s. 1% | 247.68 | 14.72 |
| P.p.e.s. 5% | 274.69 | 16.33 |
| P.p.e.s. 1% | 326.83 | 19.43 |
| C.V. | 8.28% | 8.28% |
| Res. std. dev. | 131.68 | 7.83 |
| #reps analysed | 4 | 4 |

TABLE 5

Field trials at geographic location 3

|  | Variable description | | |
|---|---|---|---|
| Variable code<br>Pedigree | VIGAB<br>1-9<br>Mean | YLD(9)<br>kg<br>Mean | YLD(9)<br>kg<br>% Checks |
| MS-B2 BC4 | 4.91 | 1914.55 | 102.88 |
| MS-B2 BC4 | 4.94 | 1932.70 | 103.85 |
| MS-B2 BC4 | 4.89 | 1952.49 | 104.92 |
| Isogenic line | 7.34 | 1783.81 | 95.85 |
| Isogenic line (50% seed density) | 7.33 | 1784.18 | 95.87 |
| Isogenic line | 7.31 | 1786.08 | 95.98 |
| Isogenic line (75% seed density) | 7.37 | 1792.20 | 96.30 |
| Isogenic line (50% seed density) | 7.33 | 1811.31 | 97.33 |
| MS-B2 BC4 | 4.90 | 1946.01 | 104.57 |
| MS-B2 BC4 × RF-BN1 + accBC3 | 5.56 | 2066.72 | 111.06 |
| MS-B2 BC4 × RF-BN2 + BC4 | 5.23 | 1690.12 | 90.82 |
| MS-B2 BC4 × RF-BN2 + BC4 | 5.19 | 1719.02 | 92.37 |
| MS-B2 BC4 × RF-BN2 + BC5 | 5.22 | 1742.14 | 93.61 |
| MS-B2 BC4 × RF-BN2 + BC5 | 5.20 | 1755.62 | 94.34 |
| MS-B2 BC4 × RF-BN1 + accBC3 | 5.98 | 1954.28 | 105.01 |
| MS-B2 BC4 × RF-BN1 RF-BN1 BC5F2 | 6.27 | 1965.55 | 105.62 |
| MS-B2 BC4 × RF-BN1 + accBC3 | 6.01 | 1996.10 | 107.26 |
| MS-B2 BC4 × RF-BN1 + accBC3 | 5.51 | 2062.47 | 110.83 |
| MS-B2 BC4 × RF-BN1 RF-BN1 BC5F2 | 5.55 | 1921.95 | 103.28 |
| Mean | 5.93 | 1853.67 | 99.61 |
| Check mean | 6.91 | 1860.98 | 100.00 |
| Signification | ** | ** | ** |
| P.p.d.s. 5% | 0.42 | 140.25 | 7.54 |
| P.p.d.s. 1% | 0.55 | 185.37 | 9.96 |
| P.p.e.s. 5% | 0.56 | 188.11 | 10.11 |
| P.p.e.s. 1% | 0.63 | 211.95 | 11.39 |
| C.V. | 5.67% | 6.17% | 6.17% |
| Res. std. dev. | 0.34 | 113.87 | 6.12 |
| #reps analysed | 4 | 4 | 4 |

TABLE 6

Field trials summary

| | AVERAGE (N = 7)<br>YIELD (G) | |
|---|---|---|
| PEDIGREE | NTR | 1 APP |
| MS-B2 × RF-BN1 | 108.1% | 113.7% |
| ISOGENIC NON-TRANSGENIC LINE | 100% | 104.5% |
| MS-B2 | 114.1% | 112.1% |
| RF-BN1 | 95.1% | 92.3% |
| CV | | |
| LSD | | 10.6% |

Example 4. Agronomic Performance of MS-B2/RF-BN1 *B. napus* Plants Compared to MS-BN1/RF-BN1 *B. napus* Plants Field trials were performed on 5 locations (4 replications/full plots) to confirm restoration and evaluate herbicide tolerance and agronomic performance of MS-B2/RF-BN1 *B. napus* hybrids in comparison with MS-BN1/RF-BN1 hybrids in the same genetic background.

Yield and vigor were determined in the absence of a glufosinate spray (A), or when treated once (B) or twice (C) with conventional applications of glufosinate (Liberty®).

The results are summarized in FIG. 1. The vigor of MS-B2/RF-BN1 hybrids is always greater than the vigor of MS-BN1/RF-BN1, whether untreated (A), treated once (B) or treated twice (C) with glufosinate ammonium.

Overall MS-B2/RF-BN1 hybrids tended to flower (start and finish) earlier and matured earlier than the MS-BN1/RF-BN1 hybrids.

Figure 2:
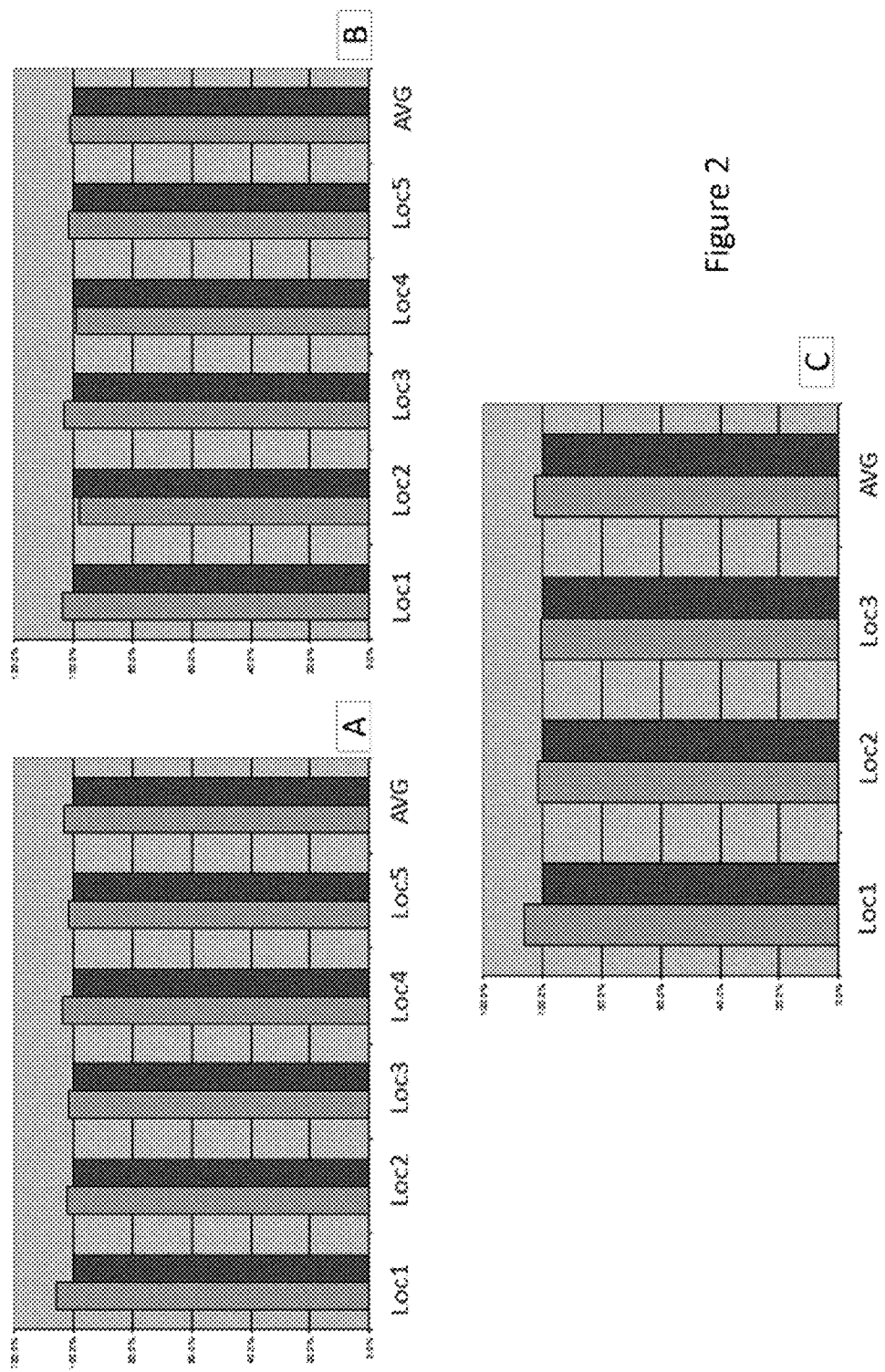
FIG. 2: Comparison of the yield after herbicide application of MS/RF hybrid *B. napus* lines. Panel A: no glufosinate ammonium application. Panel B: one glufosinate ammonium application. Panel C: two glufosinate ammonium applications. Dark gray bars: MS-BN1/RF-BN1 plants; light gray bars: MS-B2/RF-BN1 plants. Loc1 to Loc5: field trial locations; AVG: average over all locations. The yield is presented as % compared to MS-BN1/RF-BN1 plants set at 100%.

Yield was also determined for field trials of the A, B, C type described above and the results are summarized in FIG. 2 MS-B2/RF-BN1 hybrids have a 2 to 5% higher yield than MS-BN1/RF-BN1 hybrids.

It was also observed that restoration on MS-B2/RF-BN1 was complete over all genotypes and locations.

In summary, the invention is drawn at the embodiments described in the following numbered paragraphs.

1. A method for producing hybrid seed from oilseed rape plants comprising the steps of
   a. providing a male-sterile female parent oilseed rape plant comprising elite event MS-B2, reference seed comprising said elite event being deposited at the ATCC under deposit number ATCC_PTA 2485 or ATCC_PTA-850;
   b. providing a male-fertile male parent oilseed rape plant comprising elite event RF-BN1, preferably in homozygous form, reference seed comprising said elite event being deposited at the ATCC under deposit number ATCC_PTA-730;
   c. allowing pollen from said male parent oilseed rape plant to pollinate said female parent oilseed rape plant; and
   d. harvesting hybrid seed from said female parent plant.
2. The method according to paragraph 1, wherein said oilseed rape plants belong to the species *Brassica napus* or *Brassica juncea*.
3. An oilseed rape plant comprising in its nuclear genome at least one copy of elite event MS-B2, reference seed comprising said elite event being deposited at the ATCC under deposit number ATCC_PTA 2485 or ATCC_PTA-850 and at least one copy of elite event RF-BN1, reference seed comprising said elite event being deposited at the ATCC under deposit number ATCC_PTA-730.
4. The oilseed rape plant of paragraph 3, wherein said oilseed rape plants belong to the species *Brassica napus* or *Brassica juncea*.
5. A cell or tissue or seed of the oilseed rape plant of paragraph 3.
6. A pair of oilseed rape plants for use in production of hybrid seed, one of said oilseed rape plants comprising elite event MS-B2, reference seed comprising said elite event being deposited at the ATCC under deposit number ATCC_PTA 2485 or ATCC_PTA-850 and the other of said oilseed rape plants comprising elite event RF-BN1, reference seed comprising said elite event being deposited at the ATCC under deposit number ATCC_PTA-730.
7. Genomic DNA of an oilseed rape plant according to paragraph 2.
8. A *Brassica juncea* plant or plant cell comprising elite event RF-BN1, reference seed comprising said elite event being deposited at the ATCC under deposit number ATCC_PTA-730.
9. Seed from the *Brassica juncea* plant according to paragraph 5 comprising elite event RF-BN1, reference seed comprising said elite event being deposited at the ATCC under deposit number ATCC_PTA-730.
10. The plant or cell according to paragraph 8, further comprising elite event MS-B2, reference seed comprising said elite event being deposited at the ATCC under deposit number ATCC_PTA 2485 or ATCC_PTA-850.

11. Use of elite event MS-B2, reference seed comprising said elite event being deposited at the ATCC under deposit number ATCC_PTA 2485 or ATCC_PTA-850 to increase seed yield in a transgenic oilseed rape plant.
12. Use according to paragraph 11, wherein said oilseed rape plant is *Brassica juncea*.
13. A method to increase yield in oilseed rape plants comprising the step of providing said oilseed rape plant with elite event MS-B2, reference seed comprising said elite event being deposited at the ATCC under deposit number ATCC_PTA 2485 or ATCC_PTA-850.
14. A method for producing hybrid *B. juncea* seeds and plants comprising
    a. Interplanting *B. juncea* plants comprising elite event MS-B2 with *B. juncea* plants comprising elite event RF-BN1
    b. Allowing plants to cross-pollinate
    c. Harvest the seeds from the *B. juncea* plant comprising elite event MS-B2.
15. Use of a *B. juncea* plant comprising elite event RF-BN1 to produce progeny plants or to produce seeds.
16. Use of RF-BN1 to restore male fertility to a *B. juncea* plant comprising MS-B2.
17. Genomic DNA of *B. juncea* comprising RF-BN1.
18. Genomic DNA according to paragraph 17, further comprising MS-B2.
19. A *B. juncea* plant cell, plant or seed comprising in its genome a sequence having the nucleotide sequence of SEQ ID No. 5 and a sequence having the nucleotide sequence of SEQ ID No. 6, further comprising a barstar inhibitor coding sequence between said mentioned sequences.
20. The plant cell, plant or seed of paragraph 19 further comprising in its genome a sequence having the nucleotide sequence of SEQ ID No. 1 and a sequence having the nucleotide sequence of SEQ ID No. 2, further comprising a barnase inhibitor coding sequence between said mentioned sequences.
21. A method for producing hybrid *B. napus* seeds and plants comprising
    a. Interplanting *B. napus* plants comprising elite event MS-B2 with *B. napus* plants comprising elite event RF-BN1;
    b. Allowing plants to cross-pollinate;
    c. Harvest the seeds from the *B. napus* plants comprising elite event MS-B2.
22. Genomic DNA of *B. napus* comprising RF-BN1 further comprising MS-B2.
23. A *B. napus* plant cell, plant or seed comprising in its genome a sequence having the nucleotide sequence of SEQ ID No. 5 and a sequence having the nucleotide sequence of SEQ ID No. 6, further comprising a barstar inhibitor coding sequence between said mentioned sequences as well as a sequence having the nucleotide sequence of SEQ ID No. 1 and a sequence having the nucleotide sequence of SEQ ID No. 2, further comprising a barnase inhibitor coding sequence between said mentioned sequences.

The invention claimed is:

1. A method for producing hybrid seed from *Brassica* oilseed plants, comprising allowing pollen from a male-fertile male parent *Brassica* oilseed plant comprising elite event RF-BN1, reference seed comprising said elite event being deposited at the ATCC under deposit number ATCC_PTA-730, to pollinate a male-sterile female parent *Brassica* oilseed plant comprising elite event MS-B2, reference seed comprising said elite event being deposited at the ATCC under deposit number ATCC_PTA-850; and harvesting hybrid seed from said female parent plant.

2. The method according to claim 1, wherein said *Brassica* oilseed plants belong to the species *Brassica napus*.

3. A *Brassica* oilseed plant comprising in its nuclear genome at least one copy of elite event MS-B2, reference seed comprising said elite event being deposited at the ATCC under deposit number ATCC_PTA-850, and at least one copy of elite event RF-BN1, reference seed comprising said elite event being deposited at the ATCC under deposit number ATCC_PTA-730.

4. The *Brassica* oilseed plant of claim 3, wherein said *Brassica* oilseed plant belongs to the species *Brassica napus*.

5. A cell or tissue or seed of the *Brassica* oilseed plant of claim 3, wherein said cell or tissue or seed comprises in its nuclear genome at least one copy of elite event MS-B2, reference seed comprising said elite event being deposited at the ATCC under deposit number or ATCC_PTA-850, and at least one copy of elite event RF-BN1, reference seed comprising said elite event being deposited at the ATCC under deposit number ATCC_PTA-730.

6. A pair of *Brassica* oilseed plants for use in production of hybrid seed, one of said *Brassica* oilseed plants comprising elite event MS-B2, reference seed comprising said elite event being deposited at the ATCC under deposit number ATCC_PTA-850, and the other of said *Brassica* oilseed plants comprising elite event RF-BN1, reference seed comprising said elite event being deposited at the ATCC under deposit number ATCC_PTA-730.

7. Genomic DNA of a *Brassica* oilseed plant according to claim 3, comprising at least one copy of elite event MS-B2, reference seed comprising said elite event being deposited at the ATCC under deposit number ATCC_PTA-850, and at least one copy of elite event RF-BN1, reference seed comprising said elite event being deposited at the ATCC under deposit number ATCC_PTA-730.

8. A *Brassica juncea* plant or plant cell comprising elite event RF-BN1, reference seed comprising said elite event being deposited at the ATCC under deposit number ATCC_PTA-730.

9. Seed from the *Brassica juncea* plant according to claim 8, comprising elite event RF-BN1, reference seed comprising said elite event being deposited at the ATCC under deposit number ATCC_PTA-730.

10. The plant or cell according to claim 8, further comprising elite event MS-B2, reference seed comprising said elite event being deposited at the ATCC under deposit number ATCC_PTA-850.

11. The method of claim 1, wherein said elite event RF-BN1 is in homozygous form.

12. The method according to claim 1, wherein said *Brassica* oilseed plants belong to the species *Brassica juncea*.

13. The *Brassica* oilseed plant of claim 3, wherein said *Brassica* oilseed plant belongs to the species *Brassica juncea*.

* * * * *